US006444618B1

(12) United States Patent
Aven et al.

(10) Patent No.: US 6,444,618 B1
(45) Date of Patent: Sep. 3, 2002

(54) CROP PROTECTION EMULSIFIABLE CONCENTRATE CONTAINING DEFOAMING AGENTS

(75) Inventors: Michael Aven, Mainz; Friedrich Schmidt, Engelstadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/491,831

(22) Filed: Jan. 26, 2000

Related U.S. Application Data (60) Provisional application No. 60/117,931, filed on Jan. 29, 1999.

(51) Int. Cl.[7] ................................................ A01N 25/30
(52) U.S. Cl. ........................ 504/317; 504/347; 504/363; 514/237.5; 514/687; 514/937
(58) Field of Search ................. 504/363, 347, 504/317; 514/237.5, 687, 937

(56) References Cited

U.S. PATENT DOCUMENTS

| | | | |
|---|---|---|---|
| 3,912,654 A | * 10/1975 | Heid et al. .................. | 252/321 |
| 5,679,866 A | 10/1997 | Curtze et al. ................ | 568/333 |
| 5,945,567 A | 8/1999 | Curtze et al. ................ | 568/300 |
| 6,100,261 A | * 8/2000 | Sieverding ................ | 514/237.5 |

FOREIGN PATENT DOCUMENTS

| | | |
|---|---|---|
| EP | 0 407 874 | 7/1990 |
| EP | 0 447 004 | 3/1991 |
| EP | 0 727 141 A2 | 8/1996 |
| EP | 0 878 128 A1 | 11/1998 |
| WO | WO 98/00008 | 1/1998 |

OTHER PUBLICATIONS

Clariant Product Bulletin 11/98.

* cited by examiner

*Primary Examiner*—S. Mark Clardy
(74) *Attorney, Agent, or Firm*—Keil & Weinkauf (57) ABSTRACT

The novel emulsifiable concentrate (EC) formulation comprising at least one pesticidal crop protection active compound, at least one non-polar organic solvent, optionally, at least one polar aprotic cosolvent, an emulsifying surfactant system enabling an oil-in-water emulsion to be formed when the formulation is added to water, and at least one defoaming or foam breaking agent selected from the group consisting of perfluoroalkylphosphonic acids, perfluoroalkylphosphinic acids and perfluoroaliphatic polymeric esters is useful for combating pests or diseases caused by pests at a locus by treating the locus with a composition obtained from emulsifying the EC in water.

12 Claims, 1 Drawing Sheet

Figure 1

CROP PROTECTION EMULSIFIABLE CONCENTRATE CONTAINING DEFOAMING AGENTS

This application claims priority from provisional application(s) serial No. 60/117,931 filed on Jan. 29, 1999.

BACKGROUND OF THE INVENTION

Emulsifiable concentrate (EC) formulations conventionally contain an active ingredient, one or more surfactants which act as emulsifiers upon dilution of the EC with water, and a water immiscible solvent. Typical solvents for conventional EC formulations are aromatic hydrocarbons such as xylene, Shellsol A or Solvesso 200. These solvents have very low solubilities in water and are capable of dissolving a wide range of active ingredients.

Due to the presence of the solvent, many pesticides formulated as an EC have advantages such as a higher degree of systemicity and higher overall activity compared to the same pesticide formulated as a wettable powder (WP), water dispersible granule (WG) or suspension concentrate (SC).

The observed efficacy of the combination of ingredients can sometimes be significantly higher than that would be expected from the amounts of the individual ingredients used (synergism). The efficacy of the active components and handling of the spray dilution can often be improved by addition of other ingredients such as certain surfactants or defoamers.

In order to increase the ease and safety of handling and dosing of additional ingredients by the end-user, avoid unnecessary packaging material, it is desirable to develop concentrated formulations which already contain such surfactants and defoamers.

The International Patent Application WO 98/00008 discloses EC formulations containing one or more pesticides, three different kinds of non-ionic surfactants, a water-miscible cosolvent and a water-immiscible solvent. However, since no anti-foaming agent is used, it is likely that foaming would be a major problem with the dilutions of the described formulations due to the high loadings of surfactants.

Unfortunately, conventional anti-foam agents, such as silicone emulsions or silicone oils are usually not soluble in ECs.

European Patent Application EP 0 407 874 discloses aqueous crop protection formulations which contain sulfato- or sulfonato-containing surfactants and certain ammonium salts of perfluoroalkylphosphonic acids and/or perfluoroalkylphosphinic acids as foam breaking agents. However, there is no suggestion of non-aqueous EC formulations containing such foam breaking agents.

SUMMARY OF THE INVENTION

The present invention provides a novel stable non-aqueous emulsifiable concentrate (EC) formulation for crop protection active compounds which comprises
- at least one pesticidal crop protection active compound,
- at least one non-polar organic solvent,
- optionally, at least one polar aprotic cosolvent,
- an emulsifying surfactant system enabling an oil-in-water emulsion to be formed when the formulation is added to water, and
- at least one defoaming or foam breaking agent selected from the group consisting of perfluoroalkylphosphonic acids, perfluoroalkylphosphinic acids and perfluoroaliphatic polymeric esters.

These new EC formulations show excellent selective pesticidal activity in various crops.

It is thus an object of the present invention to provide novel, pesticidal EC formulations.

It is also an object of the invention to provide methods for controlling pests by contacting plants with a pesticidally effective amount of the new EC formulation.

It is another object of the invention to provide selective pesticidal compositions obtainable by emulsifying the new ECs in water.

These and other objects and features of the invention will be more apparent from the detailed description set forth hereinbelow, and from the appended claims.

DETAILED DESCRIPTION OF THE PREFERRED EMBODIMENTS

It has surprisingly been found that the stable EC formulations containing at least one pesticidal crop protection active compound, at least one non-polar organic solvent, optionally at least one polar aprotic cosolvent, an emulsifying surfactant system, and at least one defoaming or foam breaking agent selected from the group consisting of perfluoroalkylphosphonic acids, perfluoroalkylphosphinic acids and perfluoroaliphatic polymeric esters show a clearly reduced foaming behavior upon dilution with water.

In the definitions of the new EC formulations, a pesticide is a synthetic or natural compound which has the capability of inhibiting the growth of phytopathogenic fungi or of controlling a plant disease or has the capability to control undesired weeds or insects in crops. Preferably, the pesticide is selected from the group consisting of herbicides, insecticides, fungicides, bactericides, nematicides, algicides, molluscicides, virucides, compounds inducing resistance into plants, biological control agents such as viruses, bacteria, nematodes, fungi and other microorganisms, repellents of birds and animals, and plant growth regulators, or mixtures thereof.

Suitable pesticides are those which are substantially insoluble in water, but soluble in an organic solvent.

The new EC formulations contain at least one pesticide, preferably one, two or three pesticides, in particular fungicides, herbicides or insecticides.

The fungicidal compounds can be, for example, those which are capable of combating ear diseases of cereals (e.g. wheat) such as Septoria, Gibberella and Helminthosporium spp., seed and soil borne diseases, downy and powdery mildews on vines, and powdery mildew and scab on apples, etc. Mixtures of fungicidal compounds can have a broader spectrum of activity than a single compound alone. Furthermore, the mixtures of fungicides can exhibit a synergistic effect compared with the single active ingredients.

Preferred fungicides are the compounds selected from the group consisting of:

AC 382042, anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoxim-methyl, mepanipyrim, mepronil, metalaxyl, metconazole, methfuroxam, MON 65500, myclobutanil, neoasozin, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563 and zarilamid.

Moreover, the EC formulations according to the invention may contain a chemical agent that induces the systemic acquired resistance in plants such as, for example, isonicotinic acid or derivatives thereof, 2,2-dichloro-3,3-dimethylcyclopropane carboxylic acid or BION.

Many of these fungicidal compounds are described in "The Pesticide Manual," 11th Edition, The British Crop Protection Council and The Royal Society of Chemistry, 1997, (hereinbelow abbreviated as "Pesticide Manual").

Another group of preferred fungicidal compounds are the benzoylbenzenes disclosed by EP-A-0 727 141, in particular those of wherein
  $R^1$ represents a chloro atom or a methyl or trifluoromethyl group;
  $R^2$ represents a chloro atom or an alkyl, alkoxy or hydroxy group;
  $R^3$ represents a halogen atom, an optionally substituted alkyl, alkoxy, alkenyl, alkylthio, alkylsulfinyl, alkylsulfonyl, cyano, carboxy, hydroxy, nitro or an optionally substituted amino group;
  $R^4$ represents an optionally substituted alkyl group;
  $R^5$ represents an optionally substituted alkyl, alkoxy, alkenyloxy, alkynyloxy, alkylthio, cycloalkyl, cycloalkyloxy, group;

m is an integer of 1 or 2;
  $R^6$ independently represents an optionally substituted alkoxy or alkanoyloxy group; and
  $R^7$ represents a hydrogen or halogen atom or an alkyl, haloalkyl or alkoxy group.

A particularly preferred fungicide for use in the formulations of the present invention is 5-bromo-2',6-dimethyl-2,4',5',6'-tetramethoxymethoxybenzophenone, coded, as "Benzoylbenzene A" hereinbelow.

The herbicidal compounds can be, for example, compounds which possess a high herbicidal activity within a wide concentration range and/or at low dosages, and may be used in agriculture, in particular for the selective control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops such as maize and rice.

Preferred herbicides are the compounds selected from the group consisting of:

2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl, fluazifop, fluometuron, fluoroglycofen, fluridone, fluroxypyr, flurtamone, fluthiamid, fomesafen, glyphosate, halosafen, haloxyfop, hexazinone, imazamethapyr, imazamox, imazapyr, imazaquin, imazethapyr, ioxynil, isoproturon, isoxaben, isoxaflutole, lactofen, MCPA, MCPP, mecoprop, mefenacet, metabenzthiazuron, metamitron, metazachlor, methyldimron, metolachlor, metribuzin, metsulfuron, molinate, nicosulfuron, norflurazon, oryzalin, oxadiargyl, oxasulfuron, oxyfluorfen, pendimethalin, picloram, picolinafen, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr and trifluralin, in particular MCPA and pendimethalin.

Where the above mentioned herbicide is a carboxylic acid, the cited common name includes the free acid, the salts and $C_{1-10}$ alkyl esters thereof. Most preferred are the 2-ethylhexyl esters.

Mixtures of the above mentioned herbicides or mixtures of herbicides with other active ingredients like fungicides, insecticides, acaricides and nematicides a re possible.

Most of these herbicidal compounds are described in "The Pesticide Manual".

Anther group of preferred herbicidal compounds are the picolinamides disclosed by EP-A-0 447 004, in particular, those of formula II (II)

wherein

- R[8] represents a halogen atom or an alkyl, alkoxy or haloalkyl gorup;
- R[9] represents a hydrogen or halogen atom or an alkyl, alkoxy or haloalkyl group;
- R[10] represents a halogen atom, a cyano, caboxy, hydroxy or nitro group, an optionally substituted alkyl, alkenyl, alkythio, alkylsulfinyl, alkylsulfonyl, or an optionally subtituted amino group.

A particularly preferred herbicide for use in the formulations of the present invention is N-(4-fluorophenyl)-2-(3-α,α,α-trifluoromethylphenoxy)-6-pyridinecarboxamide, coded "Picolinafen" hereinbelow.

The suitable organic solvents in which the pesticide is dissolved are, as a rule, water-immiscible solvents. They are preferably selected from the group consisting of aromatic hydrocarbons, aliphatic hydrocarbons, carboxylic acid esters, alcohols, dialkylene glycol mono- or dialkyl ethers and esters of plant oils or mixtures thereof.

Aromatic and aliphatic hydrocarbons such as hexane, cyclohexane, benzene, toluene, xylene, mineral oil or kerosin or substituted naphthalenes, mixtures of mono- and polyalkylated aromatics are commercially available under the registered trademarks Solvesso®, Shellsol®, Petrol Spezial®, Plurasolv® and Exxsol®.

Esters of plant oils, which are used as nonpolar, water-immiscible solvents according to the present invention, are, as a rule, alkyl esters obtainable from medium chained fatty acids by esterification with alkanols or by transesterification of the corresponding plant oils preferably in the presence of a lipase. Preferred fatty acids of these plant oils have 5 to 20, in particular 6 to 15 carbon atoms. In a preferred embodiment the methyl ester of the plant oil used is the methyl ester of caprylic/capric ester or of capric ester having a distribution of fatty acid chain lengths of around 10 units.

Particularly preferred methyl esters of plant oils are those such as Witconol® 1095 and Witconol® 2309 which are commercially available from the Witco Corporation, Houston, USA.

The water-miscible polar aprotic solvents used as cosolvents are useful to increase the amount of active ingredient and adjuvant in the EC. Without these cosolvents, many active ingredients and many adjuvants are only soluble in relatively small amounts in the EC and the resulting formulation may show phytotoxicity due to the increased amount of solvent applied to the plant at a certain application rate of the active ingredient. Preferred polar solvents are compounds which exhibit a dielectric constant of 2.5 or more at 25° C., in particular from 2.7 to 4.0 at 25° C. Preferred are alcohols, ketones, alkylene carbonates such as ethylene carbonate and propylene carbonate, polyethylene glycols, amides, in particular, cyclic amides and lactones, as, for example, N-methylpyrrolidone, y-butyrolactone, N-cyclohexyl-pyrrolidone, and cyclohexanone. Most preferred are γ-butyrolactone and N-cyclohexyl-pyrrolidone.

In another preferred embodiment of the invention the co-solvent consists essentially of one or more, preferably two or three dimethyl dicarboxylates of formula wherein n is 2, 3 or 4.

A particularly preferred cosolvent is a mixture consisting of glutaric acid dimethyl ester, succinic acid dimethyl ester and adipic acid dimethyl ester, most preferred DBE, which is available from Lemro Chemieprodukte Michael Mrozyk KG, Grevenbroich, Germany.

The emulsifying surfactant system enabling the EC to form an oil-in-water emulsion when the formulation is added to water is a mixture of two or more surfactants, at least one of which is an anionic surfactant (a) and at least one of which is a nonionic surfactant (b).

Suitable anionic surfactants (a) may be so-called water-soluble soaps, as well as synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used. However, so-called synthetic surfactants are preferably used, especially fatty sulfonates, fatty sulfates, derivatives or alkyl aryl sulfonates. The fatty sulfates or fatty sulfonates are normally used as alkali, earth alkali or optionally substituted ammonium salts and have an alkyl moiety of 8 to 22 carbon atoms, whereby "alkyl" also means the alkyl moiety of acyl residues, such as the sodium or calcium salt of lignin sulfonic acid, of sulfuric acid dodecylate or of a mixture of fatty alcohols prepared from natural fatty acids. This also includes the salts of sulfuric acid esters, sulfonic acids and adducts of fatty alcohols and ethylene oxide. The sulfonated benzimidazole derivatives preferably contain two sulfonic acid residues and a fatty acid residue with 8 to 22 carbon atoms. Alkyl aryl sulfonates are, for example, the sodium, calcium or triethyl ammonium salts of dodecyl benzene sulfonic acid, dibutyl naphthalene sulfonic acid or of a condensate of naphthalene sulfonic acid and formaldehyde. Furthermore, phosphates, such as the salts of the phosphoric acid ester of a p-nonylphenol-(4–14)-ethylene oxide adduct or phospholipids, may be used. Most preferred anionic surfactants are the sodium, calcium or triethyl ammonium salts of dodecyl benzene sulfonic acid, in particular Rhodocal® 70/B (70% calcium dodecyl benzene sulfonate in n-butanol) and Rhodocal® 2283 (70% ammonium dodecyl benzene sulfonate) both of Rhodia GmbH (formerly Rhone-Poulenc), Phenylsulfonat CA 100 (40% calcium dodecyl benzene sulfonate in Genopol X-060 and Solvesso 200) of Clariant GmbH (formerly Hoechst AG) or Nansa® EVM 70/2E (57% linear dodecyl benzene sulfonate in 2-ethylhexanol) of Albright & Wilson.

Non-ionic surfactants (b) are preferably polyglycolether derivatives of aliphatic or cycloaliphatic alcohols, saturated or non-saturated fatty acids and alkylphenols, which have three to ten glycol ether groups and 8 to 20 carbon atoms in the (aliphatic) hydrocarbon residue and 6 to 18 carbon atoms in the alkyl residue of the alkyl phenols. Other suitable non-ionic surfactants are 20 to 250 ethylene glycol ether groups containing polyadducts of ethylene oxide and propylene oxide, ethylene diamino polypropylene glycol and alkyl polypropylene glycol with 1 to 10 carbon atoms in the alkyl moiety. The substances normally contain 1 to 5 ethylene glycol units per propylene glycol unit. Examples of non-ionic surfactants are nonylphenol polyethoxy ethanols, castor oil polyglycol ethers, polyadducts of ethylene oxide and propylene oxide, tributyl phenoxy polyethoxy ethanol, octyl phenoxy polyethoxy ethanol and tristyrylphenol ethoxylates such as Soprophor FLK (Rhodia).

Preferred are ethoxylated fatty acids such a castor or canola oil ethoxylates having at least 25, preferably 27 to 37 ethoxy units, such as Sunaptol® CA350 (castor oil ethoxylate with 35 ethoxy units) of Uniqema (formerly ICI Surfactants), Mergital® EL33 (castor oil ethoxylate with 33 ethoxy units) of Henkel KGaA, Eumulgin® C03373 (canola oil ethoxylate with 30 ethoxy units) of Henkel KGaA and Ukanil® 2507 (castor oil ethoxylate) of Uniqema.

As a rule, the surfactant system according to the present invention consists of one anionic surfactant and one or two non-ionic surfactants, preferably one of the non-ionic surfactants is a castor oil ethoxylate.

Further preferred nonionic surfactants (b) are selected from the group consisting of alcohol alkoxylates and water-immiscible N-alkyl-pyrrolidones, preferably N-$C_{3-15}$ alkyl-pyrrolidones, in particular N-octyl-pyrrolidone or N-dodecyl-pyrrolidone.

Another group of preferred nonionic surfactants (b) are alcohol alkoxylates, which are based on alkoxy units having 2 carbon atoms, thus being a mixed ethoxylate, or 2 and 3 carbon atoms, thus being a mixed ethoxylate/propoxylate. In a preferred aliphatic alcohol alkoxylate, the alkoxylate chain may have at least 5 alkoxy moieties, suitably from 5 to 25 alkoxy moieties, preferably 5 to 15, in particular 5 to 11 $C_{2-6}$ alkoxy groups. The alcohol moiety is, as a rule, derived from a $C_{9-18}$ aliphatic alcohol. Preferred alcohols are typically 50 wt.-% straight-chained and 50 wt.-% branched alcohols.

Particularly preferred are Synperonic® alcohol ethoxylates from Uniqema, in particular Synperonic® 91-6.

Further preferred alcohol alkoxylates are monobranched alcohol ethoxylates such as Atplus® MBA 11–7 (branched $C_{11}$ alcohol ethoxylate with 7 ethoxy units) of Uniqema or Genapol® X-60 (alcohol ethoxylate with 6 ethoxy units) of Clariant.

In a particularly preferred embodiment of the present invention the nonionic surfactant (b) of the inventive EC formulations comprises both one alcohol alkoxylate, in particular, Synperonic® 91-6 or Atplus® MBA 11-7 and one water-immiscible N-alkyl-pyrrolidone, in particular N-octyl-pyrrolidone or N-dodecyl-pyrrolidone.

In the preferred ECs according to the present invention, wherein the surfactant (b) consists of both one alcohol alkoxylate and one water-immiscible N-alkyl-pyrrolidone, the emulsifying surfactant system may consist of one or more non-ionic surfactants only.

These materials provide good emulsifying properties without containing alkylphenol ethoxylates, such as Synperonic® NP9 and/or the anionic derivatives thereof, for example, ethoxylated alkylaryl phosphate esters such as Rhodofac® RE 610. Alkylphenol ethoxylates and their derivatives may damage the environment due to their foaming behavior and possible oestrogenic activity.

The surfactants generally used for compositions of the invention are disclosed in publications such as:

"McCutheon's Detergents and Emulsifiers Annual", MC Publishing Corp., Ridgewood, N.J., USA 1981;

H. Stache, "Tensid-Taschenbuch", 2nd ed., C. Hanser, Munich, Vienna, 1981;

M. and J. Ash, "Encyclopedia of Surfactants", Vol. I–III, Chemical Publishing Co., New York, N.Y., USA 1980–1981.

Suitable anti-foam agents for use in the formulations of the present invention are perfluoroalkylphosphonic/perfluoroalkylphosphinic acids, in particular, mixtures comprising perfluoro-($C_{6-18}$)-alkylphosphonic acids and perfluoro-($C_{6-18}$)-alkylphosphinic acids, such as Fluowet® PL80 and, Fluowet® PP from Clariant.

Further preferred anti-foam agents are the fluoroaliphatic polymeric esters of the general formula in which n and q each independently represent an integer of 0 to 10, P represents the polymer backbone, which is preferably a co-polymer obtainable from copolymerisation of perfluoroalkyl acrylate, ethyleneoxide and propyleneoxide, and x indicates the grade of polymerisation.

Of these, most preferred for use in the present invention are fluoroaliphatic polymeric esters such as Fluorad® FC430 from 3M.

Under certain conditions, in particular when soft water is used for the tank-mix, the foam breaking properties of the perfluoroalkyl compounds alone may not be sufficient. In such cases, a second type of defoamer is incorporated into the EC formulation. Such a defoamer is preferably selected from mixtures of silica and polydialkylsiloxanes, in particular, Rhodorsil® 416 or Rhodosil® 454 from Rhone-Poulenc. Particularly preferred is a combination of polydimethylsiloxanes and perfluoroalkylphosphonic/perfluoroalkylphosphinic acids. Some cloudiness of the EC may occur due to the incorporation of the polydimethylsiloxane defoamer.

Preferred embodiments of the invention are as follows:

(i) An EC containing
10 to 900 g/L, in particular, 100 to 850 g/L of at least one pesticidal crop protection active compound,
50 to 800 g/L, in particular, 100 to 300 g/L of at least one non-polar organic solvent,
0 to 400 g/L, in particular, 0 to 250 g/L of at least one polar aprotic cosolvent,
20 to 500 g/L, in particular, 40 to 450 g/L of the emulsifying surfactant system, and
0.1 to 20 g/L, in particular, 0.2 to 10 g/L of at least one defoaming or foam breaking agent selected from perfluoro-($C_{6-18}$)-alkylphosphonic acids and/or perfluoro-($C_{6-18}$)-alkylphosphinic acids.

(ii) An EC consisting essentially of
100 to 850 g/L of at least one pesticidal crop protection active compound,
100 to 500 g/L of a solvent selected from the group consisting of diethylenglycol dialkylethers, aromatic hydrocarbons, aliphatic hydrocarbons and esters of plant oils or mixtures thereof,
0 to 250 g/L of a cosolvent selected from the group consisting of N-methylpyrrolidone, γ-butyrolactone, cyclohexanone and benzyl alcohol,
40 to 400 g/L of an emulsifying surfactant system which is a mixture of anionic and non-ionic surfactants,
0.1 to 10 g/L of at least one perfluoro-($C_{6-18}$)-alkylphosphonic acids and/or perfluoro-($C_{6-18}$)-alkylphosphinic acids, and optionally, a stabilising agent and/or antioxidant.

The solubility of the active ingredients in the formulation according to the invention depends strongly on the structure of the active ingredient. In the case of liquid active ingredients, the concentration thereof may exceed 500 g/L.

In a preferred embodiment of the present invention, the EC formulation comprises 10 to 300 g/L of one or more solid crop protection compounds; or 400 to 900 g/L of one or more liquid crop protection compounds. Most preferred are the novel ECs which comprise 10 to 100 g/L of one or more solid crop protection compound; and 450 to 850 g/L of one or more liquid crop protection compounds.

The solubility of the solid active ingredients in the formulation according to the invention depends also on the amount of the cosolvent. The relative amount of solid active ingredient soluble in the EC increases by about 40 to 60% when 10 to 15% cosolvent is incorporated into the formulation.

Another aspect of the invention is a process for the preparation of an EC as described hereinbefore, which comprises mixing all the components in a dissolver.

Further, the invention also concerns a method of combating pests at a locus which comprises treating the locus with a composition obtained from emulsifying an EC according to the invention in water.

Moreover, the invention relates to the use of an EC according to the invention as a pesticide.

As commodities, the inventive pesticidal EC formulations are in a concentrated form whereas the end-user generally employs diluted compositions. Said compositions may be diluted to concentrations down to 0.001% of active ingredient (a.i.). The doses usually are in the range of about 0.01 to 10 kg a.i./ha.

The said compositions may also comprise other auxiliaries such as chemical stabilizers, viscosity controlling agents, thickeners, adhesives, fertilizers, or other active pesticide ingredients to obtain special effects.

For a clearer understanding of the invention, specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims.

PREPARATION EXAMPLES

The registered trademarks and other designations utilized herein denote the following products:

| Ingredient | Composition | Manufacturer |
| --- | --- | --- |
| Synperonic ® 91-6 | Alcohol ethoxylate | Uniqema |
| Solventnaphtha | Aromatic hydrocarbon mixture | Shell |
| Shellsol A | Aromatic hydrocarbon mixture | Shell |
| Solvesso 200 | Aromatic hydrocarbon mixture | Exxon Chemicals |

-continued

| Ingredient | Composition | Manufacturer |
| --- | --- | --- |
| Purasolv IPL | Lactic acid isopropyl ester | Purac |
| Exxsol D110 | Aliphatic hydrocarbon mixture | Exxon Chemicals |
| Atplus ® MBA 11-7 | Monobranched alcohol ethoxylate | Uniqema |
| Atplus ® 4855B | Calcium alkylarylsulfonate, nonionic blend in an aromatic solvent | Uniqema |
| Atlox ® 3300B | Isopropylamine dodecyl benzene sulfonate | Uniqema |
| Rhodocal ® 70/B | 70% Calcium dodecyl benzene sulfonate and 30% butanol | Rhône Poulenc |
| Rhodocal ® 2283 | 70% Ammonium dodecyl benzene sulfonate in an aromatic solvent | Rhône Poulenc |
| Ukanil ® 2507 | Castor oil ethoxylate | Uniqema |
| Fluowet ® PL80 | 80% Mixture of perfluorinated phosphinic/phosphoric acids; 20% Water | Clariant |
| Fluowet ® PP | Mixture of perfluorinated phophinic/phosphoric acids | Clariant |
| CHP | Cyclohexylpyrrolidone | ISP |
| Agrimer ® AL25 | Mixture of 55% vinylpyrrolidone copolymer and 45% isopropanol | ISP |
| Eumulgin ® C03373 | Canola oil, ethoxylated, 30 EO units | Henkel KGaA |
| Phenylsulfonat CA 100 | Mixture of calcium salt of branched dodecyl benzene sulfonate, Genopol X-060, and Solvesso 200 | Clariant GmbH |
| Rhodorsil ® 467 | Silicone-polyether copolymer | Rhône Poulenc |
| Rhodorsil ® 454 | Mixture of polydimethylsiloxanes and silica | Rhône Poulenc |
| Fluorad ® FC-430 | Mixture of fluoroaliphatic esters | 3M |
| Fluorad ® FC-120 | Perfluoroalkylsulfonamide | 3M |
| Fluorad ® FC-129 | Perfluoroalkylsulfonamide | 3M |
| Fluorad ® FC-171 | Perfluoroalkylsulfonamide | 3M |
| Agsol Ex8 | N-octylpyrrolidone | ISP |
| Agsol Ex12 | N-dodecylpyrrolidone | ISP |
| DBE | Mixture of 59% glutaric acid dimethyl ester, 20% succinic acid dimethyl ester and 21% adipic acid dimethyl ester | Lemro Chemie-Produkte KG, Grevenbroich, Germany |
| Mergital EL 33 | Castor oil ethoxylate with 33 EO units | Henkel |

EXAMPLES 1 to 3

An EC formulation is prepared containing:

| | | Concentration (g/L) Example | | |
| --- | --- | --- | --- | --- |
| Component | Function | 1 | 2 | 3 |
| Picolinafen | Active Ingredient | 50 | 50 | 50 |
| MCPA 2-ethyl-hexylester | Active Ingredient | 780 | 780 | 780 |
| Atlox 4855 B | Emulsifier | 100 | 100 | 100 |
| Fluowet PL 80 | Defoamer | 0.5 | 0.5 | 0.5 |
| Solvesso 200 | Solvent | to 1 L | — | — |
| Purasolv IPL | Solvent | — | to 1 L | — |
| Exxsol D 110 | Solvent | — | — | to 1 L |

Foaming Behavior

The foaming behavior is assessed according to CIPAC Method MT 47

| Test | Example 1 | Example 2 | Example 3 |
|---|---|---|---|
| Persistant Foaming (2% in CIPAC Standard Water C) | | | |
| after 10 seconds | 7.5 mL | 10 mL | 2.5 mL |
| after 1 minute | 0 mL | 0 mL | 0 mL |
| after 3 minutes | 0 mL | 0 mL | 0 mL |
| after 12 minutes | 0 mL | 0 mL | 0 mL |

Dilutions of the formulations in CIPAC Standard Water D (2% formulation) proved to be homogeneous emulsions which were completely stable over at least 2 hours at 30° C. (CIPAC Method MT 36). The formulations showed no precipitation of solid material when they where stored over a period of 7 days at 0° C. (CIPAC Method MT 39).

EXAMPLE 4

EC formulations are prepared containing different anti-foaming agents:

| Ingredient | Concentration (g/L) |
|---|---|
| Benzoylbenzene A | 150 |
| Rhodocal 70/B | 50 |
| Ukanil 2507 | 30 |
| Synperonic 91-6 | 200 |
| Agsol Ex8 | 150 |
| γ-Butyrolactone | 200 |
| Defoamer | 1 |
| Solventnaphtha | to 1 liter |

The following anti-foaming agents have been used:

| Anti-foaming agent | Ingredient | Structure |
|---|---|---|
| AF-1 | Fluowet PL80 | perfluoroalkylphosphinic acid/ perfluoroalkylphosphonic acid |
| AF-2 | Fluorad FC-430 | Fluoroaliphatic polymeric ester |
| AF-3 | Fluorad FC-120 | Perfluoroalkylsulfonamide |
| AF-4 | Fluorad FC-129 | Perfluoroalkylsulfonamide |
| AF-5 | Fluorad FC-171 | Perfluoroalkylsulfonamide |
| AF-6 | Rhodorsil 467 | Silicone-polyether copolymer + polyether |

Foaming Behavior

Figure 1:
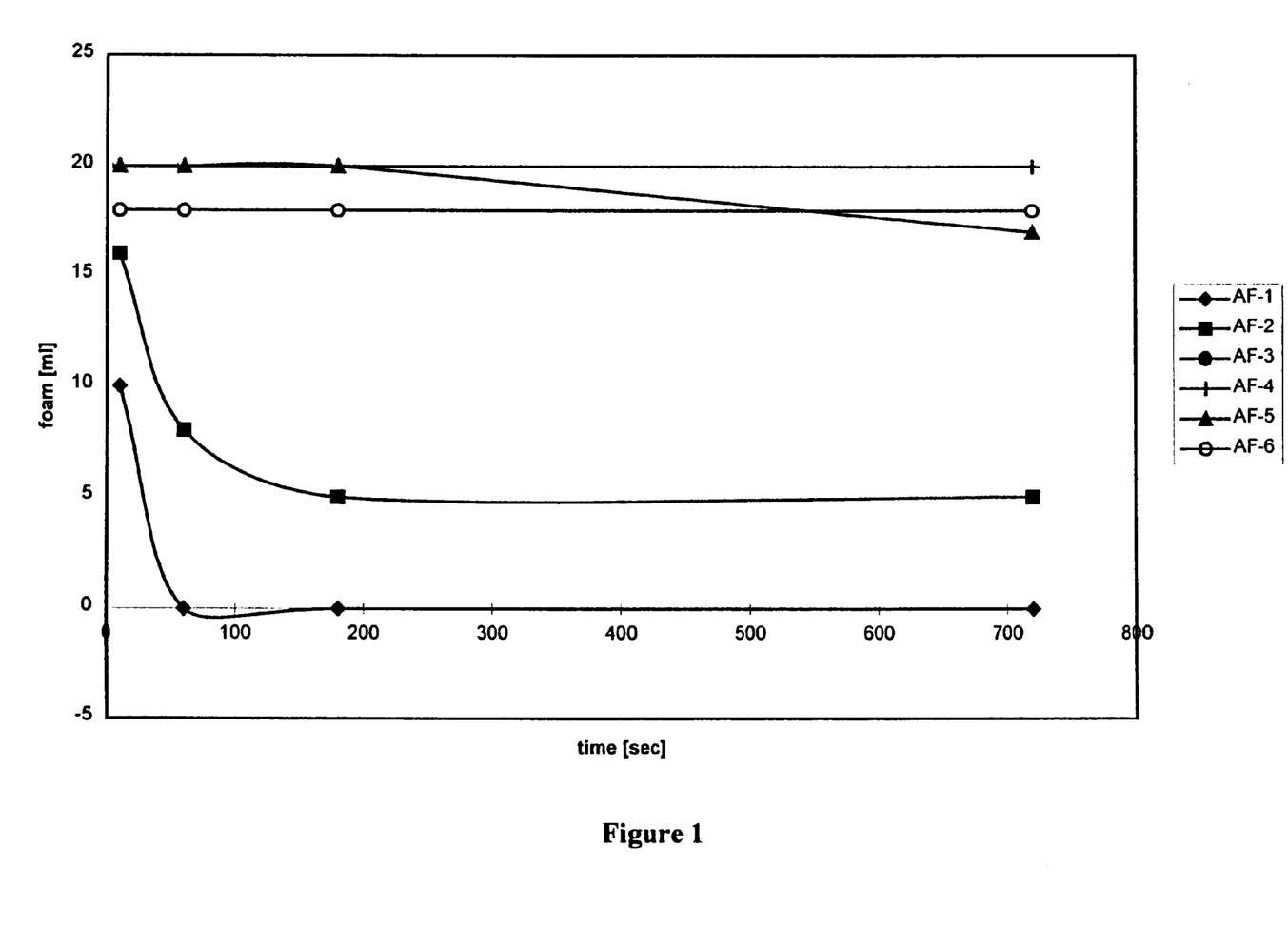
FIG. 1 is a graph showing the results of foaming behavior assessment for formulations of the present invention.

The foaming behavior is assessed according to CIPAC Method MT 47 The results of these tests are shown in the following table and in FIG. 1

| Test | AF-1 | AF-2 | AF-3 | AF-4 | AF-5 | AF-6 |
|---|---|---|---|---|---|---|
| Persistant Foaming (2% in CIPAC Standard Water C) | | | | | | |
| after 10 second | 10 mL | 16 mL | 20 mL | 20 mL | 20 mL | 18 mL |
| after 1 minute | 0 mL | 8 mL | 20 mL | 20 mL | 20 mL | 18 mL |
| after 3 minutes | 0 mL | 5 mL | 20 mL | 20 mL | 20 mL | 18 mL |
| after 12 minutes | 0 mL | 5 mL | 20 mL | 20 mL | 17 mL | 18 mL |

Dilutions of the formulations in CIPAC Standard Water D (2% formulation) proved to be homogeneous emulsions which were entirely stable over at least 2 hours at 30° C. (CIPAC Method MT 36). The formulations showed no precipitation of solid material when they where stored over a period of 7 days at 0° C. (CIPAC Method MT 39).

EXAMPLE 5

An EC formulation is prepared containing:

| Ingredient | Concentration (g/L) |
|---|---|
| Benzoylbenzene A | 150 |
| Rhodocal 70/B | 50 |
| Ukanil 2507 | 30 |
| Synperonic 91-6 | 200 |
| Agsol Ex8 | 150 |
| γ-Butyrolactone | 200 |
| Fluowet PL80 | 0.5 |
| Solventnaphtha | to 1 liter |

The resulting formulation exhibits the following physico-chemical

| Property | Example 5 |
|---|---|
| Density | 1.02 g/mL |
| Flash point | 54° C. |
| Storage of EC for 7 days 0° C. | no crystals, EC clear |

Foaming Behavior

The foaming behavior is assessed according to CIPAC Method MT 47

| Test | Example 5 |
|---|---|
| Persistant Foaming (2% in CIPAC Standard Water C) | |
| after 10 second | 10 mL |
| after 1 minute | 0 mL |
| after 3 minutes | 0 mL |
| after 12 minutes | 0 mL |

EXAMPLE 6

An EC formulation is prepared containing:

| Ingredient | Concentration (g/L) |
|---|---|
| Dimethomorph | 30 |
| Phenylsulfonat CA 100 | 50 |
| Eumulgin CO3373 | 50 |
| Atplus MBA 11-7 | 218 |

-continued

| Ingredient | Concentration (g/L) |
| --- | --- |
| γ-Butyrolactone | 218 |
| Fluowet PP | 0.5 |
| Agsol Ex12 | to 1 L |
| Density | 0.99 g/mL |

EXAMPLE 7

An EC formulation is prepared containing:

| Ingredient | Concentration (g/L) |
| --- | --- |
| Dimethomorph | 35 |
| Phenylsulfonat CA100 | 20 |
| Emulgin CO3373 | 80 |
| Synperonic 91-6 | 217 |
| γ-Butyrolactone | 217 |
| Solvesso 200 | 217 |
| Fluowet PP | 0.5 |
| Agsol Ex12 | to 1 L |
| Density | 1.01 g/mL |

EXAMPLE 8

An EC formulation is prepared containing:

| Ingredient | Concentration (g/L) |
| --- | --- |
| Pendimethalin | 330 |
| Phenylsulfonat CA100 | 80 |
| Ukanil 2507 | 20 |
| Synperonic 91-6 | 285 |
| γ-Butyrolactone | 145 |
| Solvesso 200 | 145 |
| Fluorad FC-430 | 0.5 |
| Agsol Ex12 | to 1 L |
| Density | 1.04 g/mL |

EXAMPLE 9

An EC formulation is prepared containing:

| Ingredient | Concentration (g/L) |
| --- | --- |
| Pendimethalin | 300 |
| Phenylsulfonat CA100 | 20 |
| Ukanil 2507 | 80 |
| Synperonic 91-6 | 150 |
| Solvesso 200 | 225 |
| Fluorad FCA30 | 0.5 |
| Agsol Ex12 | to 1 L |
| Density | 1.02 g/mL |

EXAMPLE 10

An EC formulation is prepared containing:

| Ingredient | Concentration (g/L) |
| --- | --- |
| Pendimethalin | 240 |
| Phenylsulfonat CA100 | 50 |
| Ukanil 2507 | 50 |
| Synperonic 91-6 | 264 |
| DBE | 198 |
| Fluowet PP | 1 |
| Agsol Ex12 | to 1 L |
| Density | 1.02 g/mL |

EXAMPLE 11

An EC formulation is prepared containing:

| Ingredient | Concentration (g/L) |
| --- | --- |
| Pendimethalin | 240 |
| Phenylsulfonat CA100 | 50 |
| Ukanil 2507 | 50 |
| Synperonic 91-6 | 330 |
| Solventnaphtha | 165 |
| Fluowet PP | 1 |
| Agsol Ex12 | to 1 L |
| Density | 1.02 g/mL |

EXAMPLE 12

An EC formulation is prepared containing:

| Ingredient | Concentration (g/L) |
| --- | --- |
| Pendimethalin | 330 |
| Phenylsulfonat CA100 | 50 |
| Ukanil 2507 | 50 |
| Synperonic 91-6 | 285 |
| Fluowet PP | 1 |
| Agsol Ex12 | to 1 L |
| Density | 1.01 g/mL |

EXAMPLE 13

An EC formulation is prepared containing:

| Ingredient | Concentration (g/L) |
| --- | --- |
| Metconazole | 90 |
| Benzoylbenzene A | 100 |
| Synperonic 91-6 | 300 |
| Phenylsulfonat CA100 | 30 |
| Mergital EL33 | 60 |
| Fluowet PL80 | 0.5 |
| Rhodorsil 454 | 0.2 g/L |
| Solventnaphtha | 175 g/L |
| γ-Butyrolactone | 170 g/L |
| Solvesso 200 | to 1 L |
| Density | 1.04 g/mL |

EXAMPLE 14

An EC formulation is prepared containing:

| Ingredient | Concentration (g/L) |
| --- | --- |
| Benzoylbenzene A | 150 |
| γ-Butyrolactone | 200 |
| Agsol Ex12 | 150 |
| Synperonic 91-6 | 200 |
| Phenylsulfonat CA100 | 87.5 |
| Ukanil 2507 | 30 |
| Fluowet PL80 | 0.5 |
| Solvesso 200 | 100 |
| Solventnaphtha | to 1 L |
| Flash point | 71° C. |
| Density | 1.04 g/mL |

EXAMPLE 15

An EC formulation is prepared containing:

| Ingredient | Concentration (g/L) |
| --- | --- |
| Benzoylbenzene A | 150 |
| γ-Butyrolactone | 200 |
| Agsol Ex12 | 150 |
| Synperonic 91-6 | 200 |
| Rhodocal 70/B | 50 |
| Ukanil 2507 | 30 |
| Fluowet PL80 | 0.5 |
| Solventnaphtha | 240 |
| Flash point | 54° C. |
| Density | 1.02 g/mL |

EXAMPLES 16 to 18

EC formulations are prepared containing:

| | Concentration (g/L) Example | | |
| --- | --- | --- | --- |
| Ingredient | 16 | 17 | 18 |
| Benzoylbenzene A | 125 | 125 | 125 |
| Metconazole | 90 | 90 | 90 |
| γ-Butyrolactone | 100 | — | — |
| Synperonic 91-6 | 300 | 300 | — |
| Atplus 871 MBA 11-7 | — | — | 300 |
| Atlox 3300B | — | 50 | 50 |
| Rhodocal 70/B | 40 | — | — |
| Ukanil 2507 | 50 | 30 | 30 |
| Fluowet PL80 | 1 | 1 | 1 |
| Agsol Ex12 | — | 150 | 150 |
| Solventnaphtha | 100 | to 1 L | to 1 L |
| Diethylenglycol dimethylether | to 1 L | — | — |

Diethylenglycol diethylether can also be used to partially replace diethylenglycol dimethylether to increase the flash point.

Physico-chemical tests

| | Example | | |
| --- | --- | --- | --- |
| Phys-chem Tests | 16 | 17 | 18 |
| Density | 1.04 g/mL | 1.00 g/mL | 1.00 g/mL |
| Flash point (blank formulation) | 55° C. | 54° C. | 60° C. |
| Foaming behavior (CIPAC MT47.1) | good self-, emuls., after inv. no stable foam | good self-, emuls., after inv. no stable foam | good self-, emuls., after inv. 2 mL stable foam |
| Spray dilution 0.5 hour | ok * | ok | ok |
| Spray dilution 1 hour | ok | ok | ok |
| Spray dilution 2 hour | ok | ok | ok |
| Spray dilution 4 hour | ok | ok | ok |

* Ok means that the composition is homogenous, exhibiting no cream or precipitate.

The EC formulations of Examples 16 to 18 combine a nonionic surfactant (alcohol ethoxylate) necessary for good performance of metconazole with a polar aprotic solvent necessary to dissolve 125 g/L of benzoylbenzene A in a water immiscible system. It is possible to raise the metconazole concentration above 90 g/L.

The new EC formulations appear as clear liquids, free from any solid material and are stable down to at least 0° C.

The spray dilutions (emulsions) are stable despite a high concentration of water miscible substances (Synperonic 91-6, γ-butyrolactone, diethylenedialkylethers). The ingredients have a good environmental profile. In the past, EC formulations containing high loadings of nonionic surfactants, in particular, Synperonic 91-6 had the tendency to cause severe foaming. The foaming behavior of all EC formulations had been assessed according to CIPAC Method MT 47. There was less than 5 ml of persistent foam upon dilution with water (1 to 2%) and 30 inversions in a 100 ml graduated cylinder filled with 100 ml water. Thus, with the aid of the anti-foam agents according to the present invention, the formation of foam in EC formulations containing nonionic surfactants can be effectively prevented.

What is claimed is:

1. A non-aqueous, emulsifiable concentrate (EC )formulation for pesticidal crop protection active compounds which comprises
   at least one pesticidal crop protection active compound,
   at least one non-polar organic solvent,
   optionally, at least one polar aprotic cosolvent,
   an emulsifying surfactant system enabling an oil-in-water emulsion to be formed when the formulation is added to water, and
   at least one defoaming or foam breaking agent selected from the group consisting of perfluoroalkylphosphonic acids, perfluoroalkylphosphinic acids and perfluoroaliphatic polymeric esters.

2. A formulation according to claim 1 comprising
   10 to 900 g/L of at least one pesticidal crop protection active compound,
   50 to 800 g/L of at least one non-polar organic solvent,
   0 to 400 g/L of at least one polar aprotic cosolvent,
   20 to 500 g/L of the emulsifying surfactant system, and
   0.1 to 20 g/L of at least one defoaming or foam breaking agent.

3. A formulation according to claim 1 wherein said pesticidal crop protection compound is selected from the group consisting of fungicides and herbicides.

4. A formulation according to claim 1 wherein said non-polar organic solvent is selected from the group consisting of dialkyleneglycol mono- or dialkylethers, aromatic hydrocarbons, aliphatic hydrocarbons and esters of plant oils or mixtures thereof.

5. A formulation according to claim 1 wherein the said cosolvent is selected from the group consisting of N-methylpyrrolidone, γ-butyrolactone, cyclohexanone and benzyl alcohol.

6. A f formulation according to claim 1 wherein said emulsifying surfactant system is a mixture of anionic and non-ionic surfactants.

7. A formulation according to claim 6 comprising at least one non-ionic surfactant selected from the group consisting of alcohol alkoxylates.

8. A formulation according to claim 7 comprising at least one $C_{9-18}$ aliphatic alcohol alkoxylated with 5 to 11 $C_{2-3}$ alkoxy groups.

9. A formulation in accordance with claim 6 comprising at least one anionic dispersant selected from the group consisting of and alkali, earth alkali or optionally substituted ammonium salts of fatty sulfonates.

10. A formulation consisting essentially of 100 to 850 g/L of at leastone pesticidal crop protection active compound, 100 to 300 g/L of a solvent selected from the group consisting of diethylenglycol dialkylethers, aromatic hydrocarbons, aliphatic hydrocarbons and esters of plant oils or mixtures thereof, 0 to 250 g/L of the cosolvent selected from the group consisting of N-methylpyrrolidone, y-butyrolactone, cyclohexanone and benzyl alcohol, 40 to 400 g/L of the emulsifying surfactant system being a mixture of anionic and non-ionic surfactants, 0.1 to 10 g/L of at least one perfluoro-$(C_{6-18})$-alkylphosphonic acids and/or perfluoro-$(C_{6-18})$-alkylphosphinic acids, and optionally a stabilising agent and/or antioxidant.

11. A formulation according to claim 1 which contains a second defoaming or foam breaking agent which is a mixture of silica and polydialkylsioxanes.

12. A method of combating pests or diseases caused by pests at a locus which comprises treating the locus with a composition obtained from emulsifying an EC formulation as defined in claim 1 in water.

* * * * *